United States Patent [19]

Tanielyan et al.

[11] Patent Number: 6,136,746
[45] Date of Patent: Oct. 24, 2000

[54] POLY-OXYANIONS AS ANCHORING AGENTS FOR METAL COMPLEXES

[75] Inventors: Setrak K. Tanielyan, Maplewood; Robert L. Augustine, Livingston, both of N.J.

[73] Assignee: Seton Hall University, South Orange, N.J.

[21] Appl. No.: 09/095,998

[22] Filed: Jun. 11, 1998

[51] Int. Cl.$^7$ ............................... B01J 31/12; B01J 31/16
[52] U.S. Cl. ........................... 502/154; 502/162; 502/164; 502/165; 502/167; 502/209; 502/210; 502/211
[58] Field of Search .................................... 502/154, 162, 502/164, 165, 167, 209, 210, 211

[56] References Cited

U.S. PATENT DOCUMENTS

| | | | |
|---|---|---|---|
| 4,448,892 | 5/1984 | Kukes et al. | 502/164 |
| 4,590,298 | 5/1986 | Che | 568/387 |
| 4,612,301 | 9/1986 | Currie et al. | 502/154 |
| 4,673,753 | 6/1987 | Siedle | 556/15 |
| 5,116,796 | 5/1992 | Edlund et al. | 502/154 |
| 5,225,598 | 7/1993 | Doumaux, Jr. et al. | 564/480 |
| 5,225,599 | 7/1993 | King et al. | 564/480 |
| 5,250,739 | 10/1993 | Mizuno et al. | 568/360 |
| 5,254,714 | 10/1993 | Ramezanian | 560/8 |
| 5,489,733 | 2/1996 | Soled et al. | 585/740 |
| 5,580,991 | 12/1996 | Sugiyama et al. | 549/325 |

OTHER PUBLICATIONS

John C. Bailar, Jr., "Heterogenizing Homogeneous Catalysts", Cat. Rev. –Sci. Eng., 10(1), 17–36 (1974).
Yusuke Izumi et al., "Catalysis of Heteropoly Acids Entrapped in Activated Carbon", Chemistry Letters, 663–666 (1981).
David C. Bailey et al., "Immobilized Transition–Metal Carbonyls and Related Catalysts", Chemical Reviews, 81(2), 109–148 (1981).
Yusuke Izumi et al., "Catalysis by Heterogeneous Supported Heteropoly Acid", Journal of Catalysis, 84, 402–409 (1983).
Hirosuki Wada et al., "Carbonylation of Olefins", Jpn. Kokai Tokkyo Koho JP 62,161,737, Chemical Abstracts, 131037, 1987.
Ronny Neumann et al., "A Ruthenium Heteropolyanion as Catalyst for Alkane and Alkene Oxidation", J. Chem. Soc. Chem. Commun., 1324–1325 (1939).
A.R. Siedle et al., "Solid–State Chemistry of Molecular Metal Oxide Clusters. Bis (triphenylphosphine) rhodium (I) Carbonyl Derivatives", Inorg. Chem., 29, 1667–1673 (1990).
Yusuke Izumi et al., "Heteropoly Anion–Modified Palladium Catalyst for Reductive Carbonylation of Nitrobenzene", Chemistry Letters, 795–796 (1990).
S. Kasztelan et al., "The Existence and Stability of the Silica–Supported 12–Molybdophosphoric Acid Keggin Unit as Shown by Raman, XPS, and $^{31}P$ NMR Spectroscopic Studies", Journal of Catalysis, 125, 45–53 (1990).
Yusuke Izumi, "Preparation of Aromatic Urethanes", Jpn. Kokai Tokkyo Koho JP 03 93,765, Chemical Abstracts, 115, 182846, 866–877 (1991).

Marco A. Schwegler et al., "Heteropolyacids as Catalysts for the Production of Phthalate Diesters", Applied Caalysis, 74, 191–204 (1991).
Taehyun Kwon et al., "Synthesis and Properties of Anionic Clays Pillared by $[XM_{12}O_{40}]^n$ Keggin Ions", Journal of Molecular Catalysis, 74, 23–33 (1992).
A.M. Trzeciak et al., "Homogeneous and Alumina Supported Rhodium Complex Catalyzed Hydrogenation", Journal of Molecular Catalysis, 88, 13–22 (1994).
Matthias Pohl et al., "Polyoxoanio–Supported Catalyst Precursors. Synthesis and Characterization of the Iridium(I) and Rhodium(I) Precatalysts $[\,(n-C_4H_9)\,_4N]_5Na_3\,[1,5-COD)M \cdot P_2W_{15}Nb_3O_{62}]$ (M = IR, Rh)", Inorg. Chem., 34, 1413–1429 (1995).
A.W. Stobbe et al, "Heteropolyanions as Redox Components in Heterogeneous Wacker Oxidation Catalysts", Journal of Catalysis, 154, 175–186 (1995).
Guo–Hua Liu et al., "Synthesis and Properties of Pillared Montmorillonite Formed by Intercalation of Transition Metal Macrocyclic Complexes", Microporous Materials, 5, 61–67 (1995).
Kam T. Wan et al., "Asymmetric Synthesis of Naproxen by a New Heterogeneous Catalyst", Journal of Catalysis, 152, 25–30 (1995).
Takafumi Shido et al., "$Rh_4$ Carbonyl Clusters Coordinated With Tris (Hydroxymethyl) phosphine Grafted Onto $SiO_2$ Surfaces and Structural Control of Active Sites in Gas–Phase Olefin Hydroformylation Reactions", Journal of Catalysis, 157, 436–449 (1995).
Patrick Gamez et al., "Homogeneous and Heterogeneous Pd–catalyzed Enantioselective Alkylation With $C_2$ –symmetric Chiral Nitrogen Ligands", Tetrahedron: Asymmetry, 6(5), 1109–1116 (1995).
Yusuke Izumi et al., "Silica–included Heteropoly Compounds as Solid Acid Catalysts", Microporous Materials, 5, 255–262 (1995).
Filippo Minutolo et al., "Polymer–Bound Chiral (Salen) Mn (III) Complex as Heterogeneous Catalyst in Rapid and Clean Enantioselective Epoxidation of Unfunctionalised Olefins", Tetrahedron Letters, 37(19), 3375–3378 (1996).
Ulrich Nagel et al., "Synthesis of Bis (phosphane) Palladium and Rhodium Complexes on a Polyethylene Oxide Grafted Polystyrene Matrix (TentaGel) and the Catalytic Behavior of the Rhodium Complexes", Chem. Ber., 129, 815–821 (1996).
Vera Isaeva et al., "Synthesis of Ru, Rh an Pd Complexes Immobilized on Modified Supports. Investigation of the Hydrogenation of Cinnamaldehyde", Bull Soc Chim Fr, 133, 351–357 (1996).

*Primary Examiner*—Sreeni Padmanabhan
*Attorney, Agent, or Firm*—Scully, Scott, Murphy & Presser

[57] ABSTRACT

A supported catalyst comprising a support, an anchoring agent such as an isopoly-oxymetal anion or oxometal salt thereof, and a metal complex which is useful in a wide variety on organic reactions, especially the hydrogenation of substituted $\alpha,\beta$ unsaturated acids and esters, is provided. Various methods of preparing the supported catalyst of the present invention is also disclosed.

38 Claims, No Drawings

POLY-OXYANIONS AS ANCHORING AGENTS FOR METAL COMPLEXES

RELATED APPLICATIONS

This application is related to copending and coassigned U.S. application Ser. No. 08/994,025, filed Dec. 18, 1997.

This patent research project was supported in part by a grant from the National Science Foundation, Grant No. CTS-9708227.

FIELD OF THE INVENTION

The present invention relates to a highly stable supported catalyst which exhibits high reactivity and selectivity in a wide variety of organic reactions. More specifically, the present invention relates to a supported catalyst which comprises a support, an anchoring agent and a metal, complex, wherein the anchoring agent is an isopoly-oxymetal anion or oxometal salt thereof. Such a supported catalyst is particularly useful for, but not limited to: the chiral hydrogenation of substituted α,β unsaturated acids or esters and α- or β-ketoesters or lactones. Various methods of preparing the supported catalyst of the present invention are also provided herein.

BACKGROUND OF THE INVENTION

Catalytic processes using either homogeneous catalysts, i.e. those present in the same phase as the reactant, or heterogeneous catalysts, i.e. those present as a separate phase in the reaction medium, have played an important role in organic synthesis. Heterogeneous catalysts are insoluble; thus they can be readily separated from the reaction mixture and, generally, offer the potential for ready re-use. Despite these advantages, prior art heterogeneous catalysts are rather limited in the number and types of organic reactions in which they can be used. In addition, they are usually less selective than homogeneous catalysts which are typically soluble metal salts or metal complexes. Indeed, homogeneous catalysts are not only more selective than heterogeneous catalysts, but have been used to promote a wider variety of organic reactions. Nevertheless, difficulties can be encountered in separating the soluble, homogeneous catalyst, both the metal and the accompanying ligands, from the product. This not only presents problems with the purity of the product, but also makes the re-use of the homogeneous catalyst problematic. The potential loss of the ligand is particularly serious in enantioselective reactions where chiral ligands are usually quite expensive.

Over the past twenty-five years, attempts have been made to "heterogenize" the more versatile homogeneous catalysts, the primary aim being to maintain reaction activity and selectivity of the homogeneous species while at the same time significantly increasing the ease of separation from the reaction medium. One such approach to achieve "heterogenization" involves reacting a metal complex or salt with a solid support such as a polymer or a metal oxide which had been previously modified by the addition of phosphine or amine ligands to the surface of the support. *Catalysis Reviews*, 16, 17–37 (1974) and *Chemical Reviews*, 81, 109 (1981) are reviews of the earlier literature concerned with polymer supported complexes. *Tetrahedron: Asymmetry*, 6, 1109–1116 (1995), *Tetrahedron Letters*, 37, 3375–3378 (1996) and *Chemische Berichte*, 129, 815–821 (1996) are examples of recent references in this area. From a practical approach, these catalysts are not widely used since their activities are frequently lower than those of the corresponding homogeneous analogs. In addition, problems associated with polymer swelling and attendant mass transport difficulties can be encountered, as well as the finding that activity is frequently lost on attempted re-use. Some success has been reported in preparing polymer supported chiral, complexes, but the selectivity observed with the use of such "heterogenized" species has generally been lower than that obtained using the homogeneous catalyst itself.

"Catalysis by Supported Complexes", *Studies in Surface Science and Catalysis,* Volume 8, Elsevier Publishing Company, Amsterdam, 1981 is an extensive review of the earlier work concerned with the anchoring of metal complexes onto surface modified oxides. *Journal of Catalysis,* 157, 436–449 (1995) and *Bulletin Societe de Chemie,* France, 133, 351–357 (1996) are some more recent references. While these materials do not manifest significant swelling problems associated with the use of polymer supports, there are frequent reports of loss of activity on attempted re-use.

In rare instances, the oxide support does not have to be modified before the application of a metal complex. *Journal of Molecular Catalysis,* 88, 13–22 (1994) describes the interaction of $Rh(OH)(CO)(PPh_3)_2$ with an alumina surface to give a supported catalyst for the hydrogenation of alkenes and benzene. This report also states that the presence of the Rh-OH entity is necessary for interaction with the surface of the alumina and that other complexes could not be attached to the oxide surface.

Another problem associated with prior art, catalysts made from metal complexes which are attached to either a modified polymer or metal oxide surface is that their preparation techniques are rather specific and are driven by the nature of the ligand to be attached. Hence, modification of the catalyst to introduce another, more selective ligand is usually an arduous and complex task, if it is one that can be accomplished at all. This circumstance has particular importance where the preparation of enantioselective catalysts are concerned since optimal enantiomeric excess is usually obtained using a specific ligand or class of ligands for a given reaction or substrate.

*Journal of Catalysis,* 152, 25–30 (1995) describes the preparation of chiral, supported aqueous-phase catalysts and their use in the preparation of naproxen. These heterogeneous catalysts have the same enantioselectivity as the homogeneous counterpart, but are 2 to 2.5 times less active.

Despite the current state of the art, there is a continuing need to develop stable heterogeneous catalysts which employ an active metal complex on an insoluble support, which catalysts are highly reactive and selective in organic reactions. Indeed, a particular need exists for the development of such catalysts which contain a chiral metal entity capable of promoting an enantioselective reaction. The term "chiral metal entity" is used herein to denote metal complexes which contain at least one chiral ligand.

SUMMARY OF THE INVENTION

One aspect of the present invention relates to a supported catalyst which comprises the following catalyst components: (i) a particulate support; e.g. an inorganic oxide or carbon; (ii) an "anchoring agent"; and (iii) a metal complex. By "anchoring agent" is meant an isopoly-oxymetal anion, i.e. a single metal polyoxide, or oxometal salt thereof. By "metal complex" is meant any catalytically active material which contains at least one transition metal atom or ion from Group IIIB, IVB, VB, VIB, VIIB, VIII, IB or IIB of the Periodic Table of Elements to which one or more ligands are attached. The ligands can be species containing, for instance, phosphorous, nitrogen, oxygen, sulfur, halogen or atoms having an electron pair, as well as carbonyls, alkenes and dienes or other moieties which can coordinate with the transition metal atom or ion.

Another aspect of the present invention relates to a method of preparing the aforementioned supported catalyst. In accordance with this aspect of the present invention, the supported catalyst is prepared by the following steps:

(i) contacting a support with an isopoly-oxymetal anion or oxometal salt thereof under conditions effective to form an isopoly-oxymetal anion-containing support;

(ii) contacting a metal complex with said isopoly-oxymetal anion-containing support under conditions effective to form a supported catalyst;

(iii) activating the catalyst by either first use in the reactor or by a reduction step such as a prehydrogenation; and (iv) optionally, recovering said supported catalyst therefrom.

In accordance with a second method of the present invention, the supported catalyst is obtained by the following steps:

(i) contacting an isopoly-oxymetal anion or oxometal salt thereof with a metal complex under conditions effective to form a solution or suspension containing said isopoly-oxymetal anion or oxometal salt thereof and said metal complex;

(ii) contacting a support with said solution or suspension prepared in step (i) under conditions effective to form a supported catalyst;

(iii) activating the catalyst by either first use in a reactor or by a reduction step such as a prehydrogenation; and (iv) optionally, recovering said supported catalyst therefrom.

Another aspect of the present invention relates to a method of forming a supported catalyst which comprises the steps of:

(i) contacting a support with an isopoly-oxymetal anion or oxometal salt thereof under conditions effective to form a modified support comprising the isopoly-oxymetal anion or oxometal salt thereof;

(ii) contacting a catalytic precursor material with said support produced in step (i) under conditions effective to form a supported catalyst precursor;

(iii) contacting the supported catalyst precursor with a ligand under conditions effective to prepare a catalytically active supported catalyst;

(iv) activating the catalyst by either first use in a reactor or by a reduction step such as prehydrogenation; and (v) optionally, recovering said supported catalyst therefrom.

In another aspect of the present invention, the supported catalyst can be used to promote a wide variety of organic reactions which include, but are not limited to: hydrogenations, dehydrogenations, isomerizations, carbonylations, hydrogenolyses, hydroformylations, oxidations, carboxylations, aminations, silylations, carboalkoxylations, cyclopropanations, alkylations, allylations, arylations and other carbon-carbon bond forming reactions. These reactions can be run in either the vapor phase or in solution. Further, they can be run in either a batch mode or in a continuous process.

Of particular importance is the use of the chiral supported catalyst of the present invention for the enantioselective hydrogenation of prochiral compounds such as substituted $\alpha,\beta$ unsaturated acids or esters and $\alpha$- or $\beta$-ketoesters or lactones.

A related process involves the use of the supported catalyst of the present invention to promote the hydroformylation of alkenes into aldehydes and/or alcohols in the presence of CO and $H_2$ under conditions which are sufficient to convert said alkene into the corresponding aldehyde and/or alcohol.

DETAILED DESCRIPTION OF THE INVENTION

As stated hereinabove, the present invention allows a homogeneous catalyst to be supported with high activity, selectivity and stability in a wide variety of organic reactions. Specifically, the catalyst of the present invention comprises the following three components: an insoluble support, an anchoring agent (an isopoly-oxymetal anion or its salt thereof), and a metal complex. The supported catalyst of the present invention is stable in air while retaining or even surpassing the activity and selectivity of the corresponding homogeneous catalyst; but, being insoluble, it is easily removed from the reaction mixture and is thus capable of extended re-use. Moreover, the supported catalyst of the present invention quite unexpectedly exhibits an increase in reactivity and selectivity after re-use. Thus, the supported catalyst of the present invention is highly useful in a wide variety of applications including, but not limited to: pharmaceutical and agrochemical applications.

The support is a particulate amorphous or crystalline material having a sufficient surface area to facilitate uniform distribution of the anchoring agent thereon. A particle size is selected to afford easy separability from the reaction media, and may typically range from 100–200 mesh.

The supported catalyst of the present invention can be made using any of the following methods. In the first method, a support is contacted with an isopoly-oxymetal anion or salt thereof under conditions which are effective to form a support which contains the isopoly-oxymetal anion or salt.

Suitable supports include, but are not limited to: metal oxides such as alumina, silica, titania, zirconia, lanthana, zeolites and clays, as well as carbon, resins, polymers and the like. The support may be used as is, or it may be treated prior to use to remove unwanted species which may adversely effect the activity of the catalyst. For example, the support may be calcined either in air or in an inert atmosphere prior to use.

The interaction between the anchoring agent and the support may be effected by reaction as discussed below; but it is to be understood that the anchoring agent may be bonded to or intercalated by the support solely by physical and/or chemical attractive forces based upon van der Waals forces, donor/acceptor interactions and other surface phenomena.

Another method of treating the support involves the use of a modifier which has been found to increase the adhesion of the isopoly-oxymetal anion or its salt to the support. Suitable modifiers that may be employed in the present invention for this purpose include, but are not limited to: metal alkoxides such as titanium alkoxide, aluminum alkoxide, silane alkoxide, vanadium alkoxide and other like metal alkoxides; polyisocyanates, hydroxy epoxides, cyano epoxides and other functionalized organic materials. Of the aforementioned modifiers, metal alkoxides are particularly preferred.

When a modifier is employed in the present invention, the modifier is contacted with the support in a solvent at a temperature of from about −25° to about 250° C. for a period of time of from about 1 min. to about 50 hrs. The amount of modifier employed in the present invention varies depending upon the type of support being employed. Typically, however, the modifier is present in about 0.01% to about 100% by weight of the support employed in the present invention.

As stated above, the support, either treated or nontreated, is then contacted with an isopoly-oxymetal anion or its salt thereof. These compounds serve as an anchoring agent or catalyst "glue." which facilitates the bonding of the metal complex to the support. The isopoly-oxymetal anions or salts thereof employed in the present invention are conventional single metal polyoxides or oxometal salts well known to those skilled in the art. The term "isopoly-oxymetal anion" is used herein to denote any single metal polyoxide or oxometal salt which is generally composed of an octahedral or tetrahedral oxometal species that contains at least one O-M-O group wherein M is a metal such as Mo, W, P or V.

It is emphasized that the isopoly-oxymetal anions employed in the present invention are different from the heteropoly acids or anions thereof described in copending U.S. application Ser. No. 08/994,025 referenced supra, in that the heteropoly acids are defined therein as being "polyprotic mixed oxides which are composed of a central ion or ions bonded to an appropriate number of oxygen atoms and surrounded by a near spherical shell of octahedral oxometal species joined together by shared oxygen atoms." The central atom of the heteroatom, which is not present in the isopoly-oxymetal anions of the present invention, is typically a cation having a +3 or +5 oxidation state.

Suitable isopoly-oxymetal anions that can be employed in the present invention include, but are not limited to: $[Mo_7O_{24}]^{6-}$, $[Mo_8O_{26}]^{4-}$, $[Mo_8O_{27}]^{6-}$, $[Mo_6O_{19}]^{2-}$, $[W_{12}O_{39}]^{6-}$, $[W_6O_{19}]^{2-}$, $[W_{12}O_{32}]^{4-}$ $VO_3$, $H_2PO_4^-$, $HPO_4^{2-}$ and other like isopoly-oxymetal anions. When present in a salt form, the cationic species used in forming the salt may be ammonium, hydrogen, alkali, alkaline earth or other suitable cations which can be present alone or in conjunction with water.

Contact of the support and the isopoly-oxymetal anion or salt thereof generally occurs in a solvent at a temperature of from about −25° to about 250° C. for a time period of from about 1 min. to about 50 hrs. Preferably, this contact occurs at a temperature of from about 25° to about 75° C. for periods of between 3 and 12 hours. Typically, in the present invention the isopoly-oxymetal anion or salt thereof is present in a weight ratio with the support of from about 0.01:1 to about 20:1. This contact step may occur in air or it may be carried out in an inert atmosphere.

In accordance with the next step of the present invention, the isopoly-oxymetal anion-containing support is contacted with a metal complex under conditions which are effective to form a supported catalyst. By "metal complex" is meant any catalytically active material which contains at least one transition metal atom or ion from Group IIIB, IVB, VB, VIB, VIIB, VIII, IB or IIB of the Periodic Table of Elements to which one or more ligands are attached. Suitable transition metal atoms or ions include: Sc, Y, Ti, Zr, Hf, V, Cr, Mo, W, Mn, Re, Fe, Ru, Os, Co, Rh, Ir, Ni, Pd, Pt, Cu, Ag, Au, Zn and the like. Preferably, the metal complex will contain a metal atom or ion from Group VIII of the Periodic Table of Elements; e.g., Fe, Ru, Os, Co, Rh, Ir, Ni, Pd and Pt.

The ligands can be species containing, for instance, phosphorus, nitrogen, oxygen, sulfur, halogen or atoms having a free electron pair, as well as carbonyls, alkenes and dienes or other moieties which can coordinate with the metal atom or ion. Suitable achiral ligands which may be employed in the present invention include, but are not limited to: species such as cyclopentadiene, carbon monoxide, cyclooctadiene (COD) and tertiary phosphines. Suitable chiral ligands which may be employed in the present invention include, but are not limited to: species such as (R,R) or (S,S) 2,2'-bis(diphenylphosphino)1,1'-binaphthyl (BINAP), (2S,3S)-bis(diphenylphosphino) butane (CHIRAPHOS), 2,3-O-isopropylidene-2,3-dihydroxy-1,4-bis(diphenylphosphino)butane (DIOP), (R,R)-1,2-bis[(2-methoxyphenyl)phenylphosphino]ethane (DIPAMP), 1,2-bis(2R,5R)-2,5-(dimethylphospholano) benzene (Me-DUPHOS) and (R) 1,2-bis (diphenylphosphino)propane (PROPHOS). Mixtures of these ligands such as (COD)(Me-DUPHOS) are also contemplated herein. The use of chiral ligands is particularly preferred in the present invention for promoting enantioselective reactions.

Examples of metal complexes contemplated by the present invention include, but are not limited to: $Rh(COD)$ $(DIPAMP)BF_4$, $Pd(R,R-BINAP)Cl_2$, $Rh(COD)$ (Me-DUPHOS)Cl and the like. In addition to metal complexes, other catalytically active compounds containing a Group VIII metal are also contemplated herein. Examples of such catalytically active compounds include, but are not limited to: the elemental Group VIII metals, Group VIII metal salts, and the like.

The contacting step between the isopoly-oxymetal anion or oxometal salt-containing support and the metal complex typically occurs in a solvent and at a temperature of from about −25° to about 250° C. for a time period of from about 1 min. to about 50 hrs. Preferably this contacting takes place at a temperature of from about 25° and about 50° C. for a time period of from about 1 hr to about 3 hrs. Generally in the present invention, the metal complex is employed at a concentration such that the metal complex to isopoly-oxymetal anion or salt thereof molar ratio is from about 0.1:1 to about 6:1; more preferably, from about 0.5:1 to about 1.5:1; and most preferably from about 0.75:1 to about 1:1.

The solvents employed in various steps of the present invention may be the same or different, and are those which are capable of dissolving the anchoring agent and/or the metal complexes. A preferred solvent is methanol, but other alcohols such as ethanol, propanol, hexanol, heptanol and the like, as well as water, ethers, esters, ketones and aliphatic or aromatic hydrocarbons, may also be employed in the present invention. The solvent may be employed as is, or it may be purified by techniques well known in the art prior to its use. For example, the solvent can be distilled and then passed over a bed or column containing an appropriate adsorbent material.

The solid supported catalyst of the present invention may then be activated either by first use in a reactor or by a reduction step such as a prehydrogenation.

The solid supported catalyst of the present invention may then be optionally recovered using techniques well known to those skilled in the art. For example, the solid catalyst may be recovered by decantation, filtration or centrifugation. The recovered solid catalyst may be used as is, or it may be washed with one of the aforementioned solvents prior to use to remove any anchoring agent or metal complex that is not bound to the support. The supported catalyst can then be dried.

In accordance with the second method of preparing the supported catalyst of the present invention, the anchoring agent mentioned hereinabove is contacted first with a metal complex to form a solution or suspension and then that solution or suspension is contacted with a support.

The contact between the anchoring agent and the metal complex typically occurs in a solvent at a temperature of from about −25° to about 250° C. for a period of time of from about 1 min. to about 50 hrs. Preferably, this contact takes place at a temperature of from about 25° to about 60° C. for a period of time of from about 15 min to about 1 hr. Generally the metal complex is employed at a concentration such that the metal complex to anchoring agent molar ratio is from about 0.1:1 to about 6:1; more preferably, from about 0.5:1 to about 1.5:1; and most preferably from about 0.75:1 to about 1:1.

The resulting solution or suspension containing the anchoring agent and the metal complex may be used as is, or, in another embodiment of the present invention, the resulting solution or suspension is dried and then slurried in a comparable solvent prior to contacting with the metal complex. The solvents employed in this embodiment of the present invention are the same as those previously mentioned hereinabove.

The solution or suspension containing the anchoring agent and metal complex is then contacted with one of the supports mentioned above. This contact between the solution or suspension and the support generally occurs in a solvent at a temperature of from about −25° to about 250° C. for a period of time from about 1 min. to about 50 hrs. Preferably, this contacting takes place at a temperature of from about 25° C. to about 60° C. for a period of time from about 3 hrs to about 12 hrs. In accordance with this aspect of the present invention, the anchoring agent and metal complex solution or suspension is present in about 0.01% to about 150% by weight of the support employed in this contacting step. The thus formed supported catalyst is, optionally, recovered as previously described.

The activation by prehydrogenation can be accomplished by stirring the supported catalyst under hydrogen typically at temperatures between ambient and 50° C. and at pressures between 1 and 10 atm. for an appropriate amount of time to achieve activation.

In accordance with another aspect of the present invention, a supported catalyst is prepared by first contacting a support with an anchoring agent as described hereinabove. The support containing the anchoring agent is then contacted with a catalyst precursor material under conditions which are effective for forming a supported catalyst precursor.

By "catalyst precursor material" is meant any metal salt or complex which is used to prepare a catalytically active entity. Examples of suitable catalyst precursors include, but are not limited to: rhodium cyclooctadiene dimer, ruthenium cyclooctadiene dimer, allyl palladium dimer, rhodium chloride and the like.

The contacting of the anchoring agent-containing support and the catalyst precursor typically occurs in a solvent at a temperature of from about −25° to about 250° C. for a time period of from, about 1 min. to about 50 hrs. Preferably this contacting takes place at a temperature of from about 25° and about 50° C. for a period of time of from about 1 hr to about 3 hrs. Generally in the present invention, the catalyst precursor material is employed at a concentration such that the precursor to anchoring agent molar ratio is from about 0.1:1 to about 6:1; more preferably, from about 0.5:1 to about 1.5:1; and most preferably from about 0.75:1 to about 1:1. The catalyst supported precursor, optionally, may be washed and dried prior to treatment with a ligand.

The thus formed catalyst supported precursor is then contacted with a ligand which forms a catalytically active entity. It is noted that the catalyst supported precursor itself may or may not be catalytically active. It is, however, converted to a catalytically active entity by contacting it with a suitable ligand. The ligands employed for this purpose include those ligands mentioned hereinabove.

The concentration of the ligand which is added to the catalyst supported precursor is typically from about 1 to about 6 mmol per mmol of catalyst precursor material. The treatment of the catalyst supported precursor and the ligand typically occurs in a solvent at temperatures of from about −25° to about 250° C. for periods of from about 1 min to about 50 hrs.

It should be mentioned that all of the above contacting steps may be conducted in air, hydrogen or in an inert gas atmosphere, as appropriate. The activation by prehydrogenation is carried out using the conditions mentioned hereinabove.

The above description illustrates the methods which can be used in forming the supported catalyst of the present invention. It is emphasized that all three catalyst components of the present invention, i.e. the support, the anchoring agent (isopoly-oxymetal anion or salt thereof), and the metal complex are needed for optimum catalytic activity, stability and selectivity. Catalysts not containing all three catalyst components of the present invention exhibit inferior results. For example, while catalysts prepared without the presence of the anchoring agent may sometimes show activity, the stability and activity in all cases is significantly lower than that of the supported catalyst of the present invention. In an appropriate solvent the isopoly-oxymetal anion-metal complex product without the support may appear to be insoluble. While this material may be used as a heterogeneous catalyst a portion of the catalytically active species does dissolve resulting in a loss of catalyst.

The supported catalyst of the present invention imparts improved catalytic properties such as catalytic activity, stability and selectivity as compared to the corresponding homogeneous catalyst or as to catalytic species prepared only from an isopoly-oxymetal anion and a metal complex. Moreover, the supported catalyst of the present invention advantageously and unexpectedly exhibits an increase in catalytic activity and selectivity when the catalyst is re-used. Without wishing to be bound by any theory it is thought that the observed increase in activity and selectivity when compared to the soluble species is the result of changes in the steric environment of the active metal in the supported moiety. Increases in stability may be brought about by the presence of the anchoring agent.

The catalyst itself comprises a relatively uniform distribution of active catalytic sites formed about the supporting particles, but remote therefrom to the extent of the selected anchoring agent bridge. This shell of active sites may typically be present at a distance, for example, 10–14 Å from the support particle itself, thereby affording excellent accessibility to reactants.

A further advantage of the supported catalyst of the present invention is that it is insoluble; and leaching of the metal, which is common with prior art supported homogeneous catalysts, is not observed.

In view of the above advantages, the supported catalyst of the present invention can be used to promote a wide variety of organic reactions which include, but are not limited to:

hydrogenations, dehydrogenations, isomerizations, carbonylations, hydrogenolyses, hydroformylations, oxidations, carboxylations, aminations, silylations, carboalkoxylations, cyclopropanations, alkylations, allylations, arylations and other carbon-carbon bond forming reactions. These reactions can be run in either the vapor phase or in solution. Further, they can be run in either a batch mode or in a continuous process using conditions well known to those skilled in the art.

In a highly preferred embodiment of the present invention, the supported catalyst of the present invention is employed in hydrogenating substituted α,β unsaturated acids or esters or other prochiral substrates. In accordance with this aspect of the present invention, a substituted α,β unsaturated acid or ester having the formula:

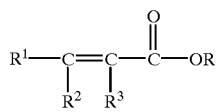

wherein $R^1$, $R^2$ and $R^3$ are the same or different and are hydrogen, alkyl containing from 1 to about 35 carbon atoms, alkenyl containing from 1 to about 35 carbon atoms, alkynyl containing from 1 to about 35 carbon atoms, aryl containing from about 6 to about 18 carbon atoms, amine, amide, or alkoxide containing from about 1 to about 35 carbon atoms, and R is hydrogen or alkyl having from about 1 to about 35 carbon atoms, is contacted with a supported catalyst of the present invention in the presence of $H_2$ under conditions which are effective to selectively hydrogenate the substituted α,β unsaturated acid or ester into a desired product. It is noted that the above substituents may be straight or branched as well as being unsubstituted or substituted with one of the substituents mentioned hereinabove. The aryl substituents may also be bicyclic or fused species.

Of particular interest is the enantioselective hydrogenation of those compounds in which $R^3$ is not hydrogen or $R^1$ is different from $R^2$ and neither is hydrogen. Hydrogenation of these prochiral substrates over a chiral supported catalyst of the present invention leads to the selective formation of one of the enantiomers of the product.

Preferred substituted α,β unsaturated acids or esters contemplated by the present invention include, but are not limited to: 2-acetamidocinnamic acid methyl ester, 2-acetamidocinnamic acid, 2-acetamidoacrylic acid methyl ester, 2-acetamidoacrylic acid, dimethylitaconate, itaconic acid, 2-methylpentenoic acid, 2-methylhexenoic acid, and 2-(6-methoxy-2-naphthyl)acrylic acid.

In another preferred embodiment of the present invention, the supported catalyst of the present invention is employed in hydrogenating carbonyl groups, particularly prochiral ketones, α-ketoesters, α-ketolactones or β-ketoesters.

The hydrogenation conditions employed in the present invention are those that are typically employed in the prior art for carrying out such a reaction.

In yet another preferred embodiment of the present invention, a process for hydroformylating alkenes into their corresponding aldehydes and/or alcohols is provided. In accordance with this aspect of the present invention, an alkene containing from 2 to about 35 carbon atoms is contacted with a supported catalyst of the present invention in the presence of $H_2$ and CO and under conditions effective to convert the alkene to the desired product. The hydroformylation reaction may be carried out in the gas phase or in the liquid phase using conditions well known to those skilled in the art.

The following examples are given to illustrate the scope of the present invention. Because these examples are given for illustrative purposes only, the invention embodied herein should not be limited thereto.

EXAMPLE I

This example illustrates a procedure for the preparation of a supported catalyst prepared in accordance with the present invention described herein above. Specifically, this example describes an impregnation method which can be utilized in the present invention for forming the supported catalysts.

Separate 25 ml glass beakers were charged with 1 g activated, neutral, gamma aluminum oxide and 66.6 micromoles of one of the isopoly-oxymetal salts listed in Table 1 below, dissolved in 7 ml ethanol:$H_2O$ (10:4 v/v). The beakers and their contents were then heated to 70° C. for about 6 hours and the slurries thus formed were stirred occasionally until the solvent evaporated. The modified supports containing the isopoly-oxymetal anion anchoring agents were then dried further overnight at 100° C.

After drying, 300 mg of the modified alumina from each beaker was transferred to separate 4 ml sample vials containing screw caps. Two (2) ml methanol and 1 ml of a methanolic solution of Rh(DIPAMP) (COD)$BF_4$ (16 micromol/ml) were introduced into each vial. The suspensions were agitated by gentle shaking overnight and the liquid was extracted and analyzed for the Rh complex using UV absorption at 290 nm to determine the extent to which the complex had adsorbed on the modified alumina supports. The solids thus obtained were washed 5 times with 5 ml portions of methanol and dried at 45° C. and 20 mm Hg. The amount of Rh complex adsorbed on each of the modified aluminas is listed in Table 1 below.

TABLE 1

Extent of Rh (DIPAMP) adsorption on modified alumina using the procedure defined in Example 1

| Isopoly-oxymetal[1] | Formula | % Rh Adsorbed |
| --- | --- | --- |
| Ammonium Molybdate | $(NH_4)_6Mo_7O_{24}\cdot 4H_2O$ | 44.4 |
| Ammonium Metatungstate | $(NH_4)_6W_{12}O_{39}\cdot H_2O$ | 56.9 |
| Ammonium Metavanadate | $NH_4VO_3$ | 20.6 |
| Ammonium $H_2$ Phosphate | $(NH_4)H_2PO_4$ | 17.5 |
| Diammonium H Phosphate | $(NH_4)HPO_4$ | 14.4 |

[1]The amount of isopoly-oxymetal modifier is 60 micromoles per gram of alumina.

EXAMPLE 2

This example illustrates a second procedure for the preparation of a supported catalyst prepared in accordance with another method of the present invention. Specifically, an in-situ process is employed in this example in synthesizing the supported catalysts.

Separate 10 ml vials were each charged with 333 mg of activated, neutral, gamma aluminum oxide and sealed with a rubber septum. The vials were evacuated and filled three times with argon. Next, 2 ml of air-free methanol was injected into each of the vials using a hypodermic syringe and the slurries thus formed were agitated for 15 minutes.

After the slurries were agitated, 20 micromol of one of the isopoly-oxymetal anchoring agents listed in Table 2, dissolved in MeOH:H$_2$O (1:1), was introduced into each of the vials and the suspension was shaken for 1 hour. Without extracting the liquid, 1 ml of Rh(DIPAMP)(COD)BF$_4$ solution (16 micromole/ml) in methanol was added to each vial and the mixtures were stirred overnight. The supernatant liquids from each vial were removed using a gas-tight syringe and analyzed for the Rh complex using UV absorption at 290 nm. The solid materials were washed. repeatedly with 5 ml portions of methanol until no color was observed in the wash liquid and then evacuated until dry at room temperature. The catalyst samples were stored in the closed vials until use.

TABLE 2

Extent of RH (DIPAMP) adsorption on isopoly-oxymetal modified alumina using the procedure of Example 2.

| Isopoly-oxymetal[1] | Formula | % Rh Adsorbed |
| --- | --- | --- |
| Ammonium Molybdate | (NH$_4$)$_6$Mo$_7$O$_{24}$.4H$_2$O | 30.0 |
| Ammonium Metatungstate | (NH$_4$)$_6$W$_{12}$O$_{39}$.H$_2$O | 88.8 |
| Ammonium Metavanadate | NH$_4$VO$_3$ | 6.9 |
| Ammonium H$_2$ Phosphate | (NH$_4$)H$_2$PO$_4$ | 7.5 |
| Diammonium H Phosphate | (NH$_4$)HPO$_4$ | 0 |

[1]No analysis was performed for the amount of adsorbed isopoly-oxymetal modifier. It was assumed to be 20 micromole per 330 mg aluminum oxide.

EXAMPLE 3

In this example, the catalytic activity in the chiral hydrogenation of methyl 2-acetamidoacrylate was investigated for each of the catalysts prepared in Examples 1 and 2. Specifically, the hydrogenations were run in a constant volume, constant pressure volumetric system. The glass autoclave utilized for these experimentations was a jacketed reaction flask with #25 Ace-thread (Ace Glass Inc.) equipped with a modified magnetic stirrer which was designed so that there was no direct contact between the stirring blades and the bottom of the reactor. This ensured that the catalyst particles were not crushed during the hydrogenation run.

In a typical run, the reactor was charged with 330 mg of catalyst prepared in accordance with Example 1 or 2 and the system was evacuated and filled with argon three times. Fourteen (14) ml of air-free methanol was injected through the septum and the argon was replaced with hydrogen by two evacuation-fill cycles. After stirring was initiated, 1 ml of a methanolic solution of methyl 2-acetamidoacrylate (50 mg/ml) was introduced using a gas-tight syringe and hydrogen uptake at 25° C. and 760 mm Hg pressure was recorded using a computer interfaced with the reactor system. After the reaction had run for two hours, the reaction was stopped and the product mixture was analyzed by GC using a chiral β-TA cyclodextrin column at 110° C. The product enantiomeric excess (ee) and percent conversion are listed in Table 3 below.

TABLE 3

Product enantiomeric excess (ee) and percent conversion in the hydrogenation of methyl 2-acetamidoacrylate over RH(DIPAMP) catalysts supported on isopoly-oxymetal modified aluminum.

| | Example 1 Catalysts | | Example 2 Catalyst | |
| --- | --- | --- | --- | --- |
| Isopoly-Oxymetal | ee (%) | Rate ($\times 10^3$)[1] | ee (%) | Rate ($\times 10^3$)[1] |
| (NH$_4$)$_6$Mo$_7$O$_{24}$.4H$_2$O | 95.4 | 1.6 | — | 0.0 |
| (NH$_4$)$_6$W$_{12}$O$_{39}$.H$_2$O | — | 0.0 | — | 0.0 |
| NH$_4$VO$_3$ | 91.4 | 0.3 | — | 0.0 |
| (NH$_4$)H$_2$PO$_4$ | 92.4 | 0.2 | — | 0.0 |
| (NH$_4$)$_2$HPO$_4$ | 92.4 | 0.2 | — | 0.0 |

[1]moles H$_2$/mole of Rh/min.

In all of the previous hydrogenations, the isopoly-oxymetal:Rh molar ratio was 1:1. In Table 4 below are listed the rates of hydrogenation and product ee's found for methyl 2-acetamidoacrylate hydrogenations using as the catalyst aluminum/ammonium metatungstate supported Rh(DIPAMP) complexes with different tungstate:Rh ratios. These hydrogenations were run using the same conditions and amounts described hereinabove.

TABLE 4

Product enantiomeric excess (EE) and percent conversion in the hydrogenation of methyl 2-acetamidoacrylate over Rh (DIPAMP) catalysts supported on ammonium metatungstate alumina with different tungstate:Rh ratios.

| Tungstate:Rh ratio | Preparation Procedure | Rate ($\times 10^3$)[1] | Product ee |
| --- | --- | --- | --- |
| 1:1.6 | Example 2 | 0.1 | 81% |
| 1:3 | Example 1 | 0.9 | 86% |

[1]moles H$_2$/mole of Rh/min.

While the invention has been particularly shown and described with respect to preferred embodiments thereof, it will be understood by those, skilled in the art that the foregoing and other changes in form and detail may be made without departing from the spirit and scope of the invention.

What is claimed is:

1. A supported catalyst comprising a support, an anchoring agent, and a metal complex, wherein the anchoring agent is an isopoly-oxymetal anion or its salt thereof.

2. The supported catalyst of claim 1 wherein said support is selected from the group consisting of metal oxides, carbon, resins and polymers.

3. The supported catalyst of claim 2 wherein the metal oxide is selected from the group consisting of alumina, silica, titania, lanthana, zeolites and clays.

4. The supported catalyst of claim 1 wherein the support is a treated support.

5. The supported catalyst of claim 4 wherein said treated support material is obtained by calcining said support or contacting said support with a modifier.

6. The supported catalyst of claim 5 wherein the modifier is a metal alkoxide.

7. The supported catalyst of claim 6 wherein said metal alkoxide is titanium alkoxide, aluminum alkoxide, silane alkoxide or vanadium alkoxide.

8. The supported catalyst of claim 1 wherein said isopoly-oxymetal anion is an anion selected from the group consisting of $[Mo_7O_{24}]^{6-}$, $[Mo_8O_{26}]^{4-}$, $[MO_8O_{27}]^{6-}$, $[MO_6O_{19}]^{2-}$, $[W_{12}O_{39}]^{6-}$, $[W_6O_{19}]^{2-}$, $[W_{12}O_{32}]^{4-}$, $VO_3^-$, $H_2PO_4^-$ and $HPO_4^{2-}$.

9. The supported catalyst of claim 8 wherein said isopoly-oxymetal anion further contains a cationic species selected from the group consisting of ammonium, hydrogen, $H_2O$, alkali, alkaline earth and mixtures thereof.

10. The supported catalyst of claim 1 wherein the metal complex is a catalytically active material which contains at least one metal atom or ion from Group IIIB, IVB, VB, VIB, VIIB, VIII, IB or IIB of the Periodic Table of Elements to which one or more ligands are attached.

11. The supported catalyst of claim 10 wherein said metal atom or ion is from Group VIII of the Periodic Table of Elements.

12. The supported catalyst of claim 10 wherein said ligand is selected from the group consisting of phosphines, amines, carbonyl, alkenes, dienes, halides, (R,R) or (S,S)2,2'-bis(diphenylphosphino)-1,1'-binapthyl(BINAP), (2S, 3S)-bis(diphenylphosphino)butane (CHIRAPHOS), cyclooctadiene (COD), (R,R)-1,2-bis[(2 methoxyphenyl)phenylphosphine]ethane (DIPAMP), 1,2-bis(2R,5R)-2,5 (dimethylphospholano)benzene (Me-DUPHOS), (R)1,2-bis(diphenylphosphino)propane (PROPHOS), 2,3-O-isopropylidene-2,3-dihydroxy-1,4-bis(diphenylphosphino)butane (DIOP)and mixtures thereof.

13. A method of preparing the supported catalyst of claim 1 comprising:
   (i) contacting a support with an isopoly-oxymetal anion or salt thereof under conditions effective to form an isopoly-oxymetal anion or oxometal salt-containing support;
   (ii) contacting a metal complex with said isopoly-oxymetal anion or oxometal salt-containing support under conditions effective to form a supported catalyst; and
   (iii) optionally, recovering said supported catalyst.

14. The method of claim 13 wherein step (i) occurs in a solvent at a temperature of from about −25° to about 250° C. for a period of time of from about 1 min. to about 50 hrs.

15. The method of claim 13 wherein said isopoly-oxymetal anion or oxometal salt is present in a weight ratio of about 0.01:1 to about 20:1 with the support employed in step (i).

16. The method of claim 13 wherein said support is calcined or treated with a metal alkoxide prior to step (i).

17. The method of claim 16 wherein the metal alkoxide is selected from the group consisting of titanium alkoxide, aluminum alkoxide, silane alkoxide and vanadium alkoxide.

18. The method of claim 13 wherein step (ii) occurs in a solvent at a temperature of from about −25° to about 250° C. for a period of time of from about 1 min. to about 50 hrs.

19. The method of claim 13 wherein said metal complex is contacted at a concentration to provide a molar ratio of said metal complex to said isopoly-oxymetal anion or oxometal salt of from about 0:1:1 to about 6:1.

20. The method of claim 13 wherein said recovering step includes decantation, filtration and/or centrifugation.

21. A method of preparing the supported catalyst of claim 1 comprising:
   (i) contacting an isopoly-oxymetal anion or oxometal salt thereof with a metal complex under conditions effective to form a mixture or suspension containing said isopoly-oxymetal anion or oxometal salt thereof and said metal complex;
   (ii) contacting a support with said solution or suspension formed in step (i) under conditions effective to form a supported catalyst; and
   (iii) optionally, recovering said supported catalyst.

22. The method of claim 21 wherein step (i) occurs in a solvent at a temperature of from about −25° to about 250° C. for a period of time of from about 1 min. to about 50 hrs.

23. The method of claim 21 wherein said metal complex is used at a concentration to provide a molar ratio of said metal complex to said isopoly-oxymetal anion or oxometal salt thereof of from about 0:1:1 to about 6:1.

24. The method of claim 21 wherein said support is calcined or treated with a metal alkoxide prior to step (ii).

25. The support of claim 24 wherein said metal alkoxide is selected from the group consisting of titanium alkoxide, aluminum alkoxide, silane alkoxide and vanadium alkoxide.

26. The method of claim 21 wherein step (ii) occurs in a solvent at a temperature of from about −25° to about 250° C. for a period of time of from about 1 min. to about 50 hrs.

27. The method of claim 21 wherein said solution or suspension containing said isopoly-oxymetal anion or oxometal salt thereof and metal complex is present in a weight ratio of about 0.01:1 to about 20:1 with the support employed in step (ii).

28. The method of claim 21 wherein said recovering step includes decantation, filtration and/or centrifugation.

29. A method of preparing the supported catalyst of claim 1 comprising:
   (i) contacting a support with an isopoly-oxymetal anion or salt thereof under conditions effective to form an isopoly-oxymetal anion or oxometal salt-containing support;
   (ii) contacting said isopoly-oxymetal anion or salt-containing support with a catalyst precursor material under conditions effective to form a catalyst supported precursor; and
   (iii) contacting said catalyst supported precursor with a ligand which is capable of transforming the catalyst supported precursor to a catalytic active entity; and
   (iv) optionally, recovering said catalytic active entity.

30. The method of claim 29 wherein said support is calcined or treated with a metal alkoxide prior to use.

31. The method of claim 30 wherein the metal alkoxide is selected from the group consisting of titanium alkoxide, aluminum alkoxide, silane alkoxide and vanadium alkoxide.

32. The method of claim 29 wherein step (i) occurs in a solvent at a temperature of from about −25° to about 250° C. for a period of time of from about 1 min. to about 50 hrs.

33. The method of claim 29 wherein said catalyst precursor material is a metal salt or complex from which a catalytically active entity can be prepared.

34. The method of claim 33 wherein the metal salt or complex of said catalyst precursor material is selected from the group consisting of rhodium cyclooctadiene dimer, ruthenium cyclooctadiene dimer, allyl palladium dimer and rhodium chloride.

35. The method of claim 29 wherein step (ii) occurs in a solvent at a temperature of from about −25° to about 250° C. for a period of time from about 1 min. to about 50 hrs.

36. The method of claim 29 wherein said ligand is selected from the group consisting of, phosphines, amines, carbonyl, alkenes, dienes, halides, (R,R) or (S,S)2,2'-bis(diphenylphosphino)-1,1'-binapthyl(BINAP), (2S, 3S)-bis(diphenylphosphino)butane (CHIRAPHOS), cyclooctadiene (COD), (R,R)-1,2-bis[(2-methoxyphenyl)phenylphosphine]ethane (DIPAMP), 1,2-bis(2R,5R)-2,5 (dimethylphospholano)benzene (Me-DUPHOS) (R)1,2-bis(diphenylphosphino)propane (PROPHOS), 2,3-O-isopropylidene-2,3-dihydroxy-1,4-bis(diphenylphosphino)butane (DIOP)and mixtures thereof.

37. The method of claim 29 wherein step (iii) occurs in a solvent at a temperature of from about −25° to about 250° C. for a period of time of from about 1 min. to about 50 hrs.

38. The method of claim 29 wherein from about 1 to about 6 mmol of said ligand per mmol of catalyst precursor material is employed in step (iii).

* * * * *